US00PP17430P2

(12) United States Plant Patent
Head et al.

(10) Patent No.: US PP17,430 P2
(45) Date of Patent: Feb. 20, 2007

(54) ***OPHIOPOGON* PLANT NAMED 'HOCF'**

(50) Latin Name: *Ophiopogon jaburan*
Varietal Denomination: HOCF

(75) Inventors: Robert Harold Head, Seneca, SC (US); Lisa Jones Head, Seneca, SC (US); William A. Head, Walhalla, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 11/188,963

(22) Filed: Jul. 25, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Ophiopogon* plant named 'HOCF' characterized by its upright and somewhat outwardly arching plant habit; freely clumping habit; large dark-green colored foliage; long racemes with numerous white-colored flowers; numerous large violet blue-colored fruits; and resistance to *Anthracnose*.

3 Drawing Sheets

Botanical designation: *Ophiopogon jaburan.*
Cultivar denomination: 'HOCF'.

BACKGROUND OF THE INVENTION

The present Invention relates to a new and distinct cultivar of *Ophiopogon* plant, botanically known as *Ophiopogon jaburan,* and hereinafter referred to by the cultivar name HOCF.

The new *Ophiopogon* is a product of a planned breeding program conducted by the Inventors in Seneca, S.C. The objective of the breeding program is to create new *Ophiopogon* cultivars with larger leaves, larger flowers, cold hardiness and disease resistance.

The new *Ophiopogon* originated from a self-pollination made by the Inventors in Seneca, S.C. in 1990 of an unnamed selection of *Ophiopogon jaburan,* not patented. The cultivar HOCF was discovered and selected by the Inventors as a single plant within the progeny of the stated self-pollination in a controlled environment in Seneca, S.C. in 1993.

Asexual reproduction of the new cultivar by divisions in Seneca, S.C. since March, 1995, has shown that the unique features of this new *Ophiopogon* are stable and reproduced true to type in successive generations.

SUMMARY OF THE INVENTION

Plants of the cultivar HOCF have not been observed under all possible environmental conditions. The phenotype may vary somewhat with variations in environment such as temperature and light intensity without, however, any variance in genotype.

The following traits have been repeatedly observed and are determined to be the unique characteristics of 'HOCF'. These characteristics in combination distinguish 'HOCF' as a new and distinct cultivar:

1. Upright and somewhat outwardly arching plant habit.
2. Freely clumping habit.
3. Large dark-green colored foliage.

4. Long racemes with numerous white-colored flowers.
5. Numerous large violet blue-colored fruits.
6. Resistant to *Anthracnose.*

Plants of the new *Ophiopogon* can be compared to plants of the parent, the unnamed selection of *Ophiopogon jaburan.* In side-by-side comparisons conducted in Seneca, S.C., plants of the new *Ophiopogon* differed from plants of the parent selection in the following characteristics:

1. Plants of the new *Ophiopogon* had larger and darker green-colored leaves than plants of the parent selection.
2. Plants of the new *Ophiopogon* developed larger clumps than plants of the parent selection.
3. Plants of the new *Ophiopogon* had longer flower racemes with larger and more flowers per raceme than plants of the parent selection.
4. Plants of the new *Ophiopogon* had outwardly arching and dropping flower scapes whereas plants of the parent selection had upright flower scapes.
5. Plants of the new *Ophiopogon* produced larger and more fruits per flower than plants of the parent selection.
6. Plants of the new *Ophiopogon* and the parent selection differed in fruit coloration.
7. Plants of the new *Ophiopogon* were more cold hardy than plants of the parent selection.

Plants of the new *Ophiopogon* can be compared to plants of the *Ophiopogon jaburan* cultivar Vittatus (non patented). In side-by-side comparisons conducted in Seneca, S.C., plants of the new *Ophiopogon* differed from plants of the cultivar Vittatus in the following characteristics:

1. Plants of the new *Ophiopogon* had longer and narrower leaves than plants of the cultivar Vittatus.
2. Plants of the new *Ophiopogon* had dark green-colored leaves whereas plants of the cultivar Vittatus had green and white variegated leaves.
3. Plants of the new *Ophiopogon* were stronger and longer-lived than plants of the cultivar Vittatus.
4. Plants of the new *Ophiopogon* had more and longer flower scapes, longer flower racemes and more flowers per raceme than plants of the cultivar Vittatus.

5. Plants of the new *Ophiopogon* produced larger and more fruits per flower than plants of the cultivar Vittatus.
6. Plants of the new *Ophiopogon* and the cultivar Vittatus differed in fruit coloration.
7. Plants of the new *Ophiopogon* were more cold hardy than plants of the cultivar Vittatus.

Plants of the new *Ophiopogon* can also be compared to plants of the *Ophiopogon planiscapus* cultivar Nigrecens (non patented). In side-by-side comparisons conducted in Seneca, S.C., plants of the new *Ophiopogon* differed from plants of the cultivar Nigrecens in the following characteristics:

1. Plants of the new *Ophiopogon* had larger leaves than plants of the cultivar Nigrecens.
2. Plants of the new *Ophiopogon* had dark green-colored leaves whereas plants of the cultivar Nigrecens had dark blue to almost black-colored leaves.
3. Plants of the new *Ophiopogon* produced larger clumps than plants of the cultivar Nigrecens.
4. Plants of the new *Ophiopogon* had more and longer flower scapes, longer flower racemes and more flowers per raceme than plants of the cultivar Nigrecens.
5. Plants of the new *Ophiopogon* produced larger fruits than plants of the cultivar Nigrecens.
6. Plants of the new *Ophiopogon* and the cultivar Nigrecens differed in fruit coloration.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Ophiopogon*.

The photograph on the first sheet is a side perspective view of typical two-year old flowering plants of the new *Ophiopogon* grown in a container.

The photograph on the second sheet is a side perspective view of a typical four-year old plant of 'HOCF' with fruits grown in a container.

The photograph on the third page is a close-up view of a typical inflorescence of 'HOCF'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Seneca, S.C. in one-quart containers and ground beds in an outdoor nursery and under conditions which closely approximate commercial production conditions. During the production of the plants, day temperatures ranged from −5° C. to 40° C. and night temperatures ranged from −20° C. to 35° C. Plants were grown under 50 percent shade. Plants used for the description were about three years old.

Botanical classification: *Ophiopogon jaburan* cultivar HOCF.

Parentage: Self-pollination of an unnamed selection of *Ophiopogon jaburan* selection, not patented.

Propagation:

*Type cutting.*—By divisions.

*Time to produce a rooted young plant, summer.*—About three months at 32° C.

*Time to produce a rooted young plant, winter.*—About six months at 18° C.

*Root description.*—Thick, coarse, fibrous; 156D in color.

*Rooting habit.*—Freely branching; dense.

Plant description:

*Plant form/growth habit.*—Upright and outwardly arching flowering plant. Long-lived perennial plant. Plants tufted or cespitose with basal leaves and central flowering scapes with flowers arranged in long drooping racemes. Freely clumping habit, about three to six basal off-shoots are produced each growing season. Vigorous growth habit.

*Crop time.*—From divisions, usually about 12 to 15 months are required to produce finished flowering plants in containers.

*Plant height, soil level to top of foliar plane.*—About 40 to 90 cm.

*Plant width.*—About 40 to 80 cm.

*Leaves.*—Arrangement: Simple; basal; sessile. Length: About 79 cm. Width: About 1.8 cm. Shape: Linear. Apex: Rounded subulate. Base: Cuneate. Margin: Entire. Texture, upper surface: Glabrous, smooth; relatively thick and leathery. Texture, lower surface: Glabrous, fluted; relatively thick and leathery. Venation pattern: Parallel. Color: Developing leaves, upper surface: 141A. Developing leaves, lower surface: 137B. Fully expanded leaves, upper surface: 131A. Fully expanded leaves, lower surface: 137A. Venation, upper and lower surfaces: 137B.

Flower description:

*Flowering habit.*—Inflorescences scapose with single campanulate flowers; flowers arranged in long racemes on long, outwardly arching and drooping scapes. Flowers not fragrant; flowers not persistent. Flowers face mostly downward.

*Natural flowering season.*—Plants flower in the late summer in South Carolina.

*Flower longevity on the plant.*—About four days.

*Inflorescence size.*—Length: About 12 to 15 cm. Width: About 3 to 4 cm.

*Flower buds.*—Length: About 7.5 to 9 mm. Diameter: About 4.5 to 5 mm. Shape: Urceolate. Color: 155C.

*Flowers.*—Quantity of flowers per inflorescence: Freely flowering, about 100 to 120. Shape: Campanulate. Diameter: About 1.2 cm. Depth (height): About 8 cm.

*Petals.*—Quantity: Three per flower. Length: About 8 mm. Width: About 2.5 mm. Shape: Ovate. Apex: Rounded and keel-shaped. Margin: Entire. Texture, upper and lower surfaces: Smooth, glabrous; thick and waxy. Color: When opening, upper surface: 155C. When opening, lower surface: 155A. Fully opened, upper surface: 157C; color becoming closer to 159C with development. Fully opened, lower surface: 155A. Depth (height): About 8 cm.

*Sepals.*—Quantity: Three per flower; fused. Length: About 6.5 mm. Tube diameter: About 1.5 mm. Shape: Ovate. Apex: Rounded. Margin: Entire. Texture, upper and lower surfaces: Smooth, glabrous; thick and waxy. Color: When opening and fully opened, upper surface: 155C. When opening and fully opened, lower surface: Close to 155C.

*Scape.*—Angle: About 30° to 60° from vertical. Strength: Strong; flexible. Length: About 55 to 65 cm. Diameter: About 7.5 mm. Texture: Fluted, glabrous; thick and leathery. Color: 144A.

*Pedicels.*—Angle: About 30° to 90° from raceme axis. Strength: Strong; flexible. Length: About 1 cm. Diameter: About 0.6 mm. Texture: Fluted, glabrous. Color: 144B.

*Reproductive organs.*—Stamens: Quantity per flower: Six. Anther shape: Lanceolate. Anther length: About 4 mm. Anther diameter: About 0.7 to 1 mm. Anther color: 151C. Amount of pollen: Abundant. Pollen color: 151C. Pistils: Quantity per flower: One. Length: About 4 to 5 mm. Stigma shape: Botuliform. Stigma color: 151A. Style length: About 6 mm. Style color: 155A. Ovary color: 155C.

*Fruits.*—Quantity per flower: One to three. Length: About 9 to 14 mm. Diameter: About 8 to 11 mm. Texture: Smooth, waxy. Color: 95B.

*Seeds.*—Quantity per fruit: One. Length: About 9 to 11 mm. Diameter: About 6 to 9 mm. Color: 155C.

Disease/pest resistance: Plants of the new *Ophiopogon* have been observed to be resistant to *Anthracnose*. Resistance to pests and other pathogens common to *Ophiopogon* has not been determined.

Temperature tolerance: Plants of the new *Ophiopogon* have been observed to tolerate high temperatures of 40° C. and have been observed to be hardy to USDA Zone 6B.

It is claimed:

1. A new and distinct cultivar of *Ophiopogon* plant named 'HOCF', as illustrated and described.

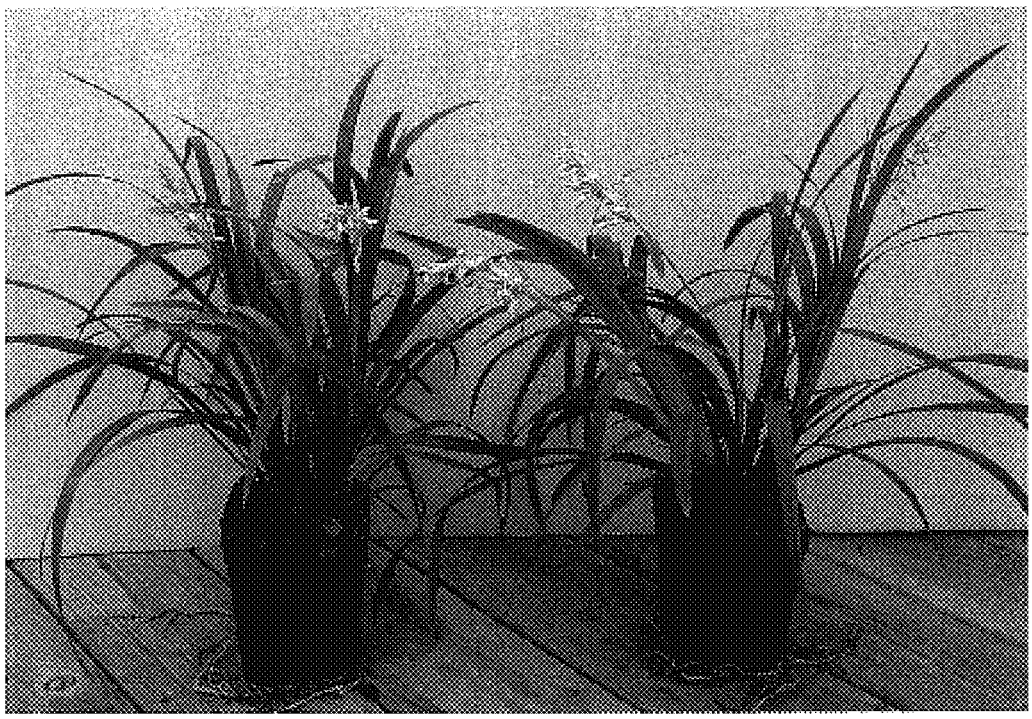

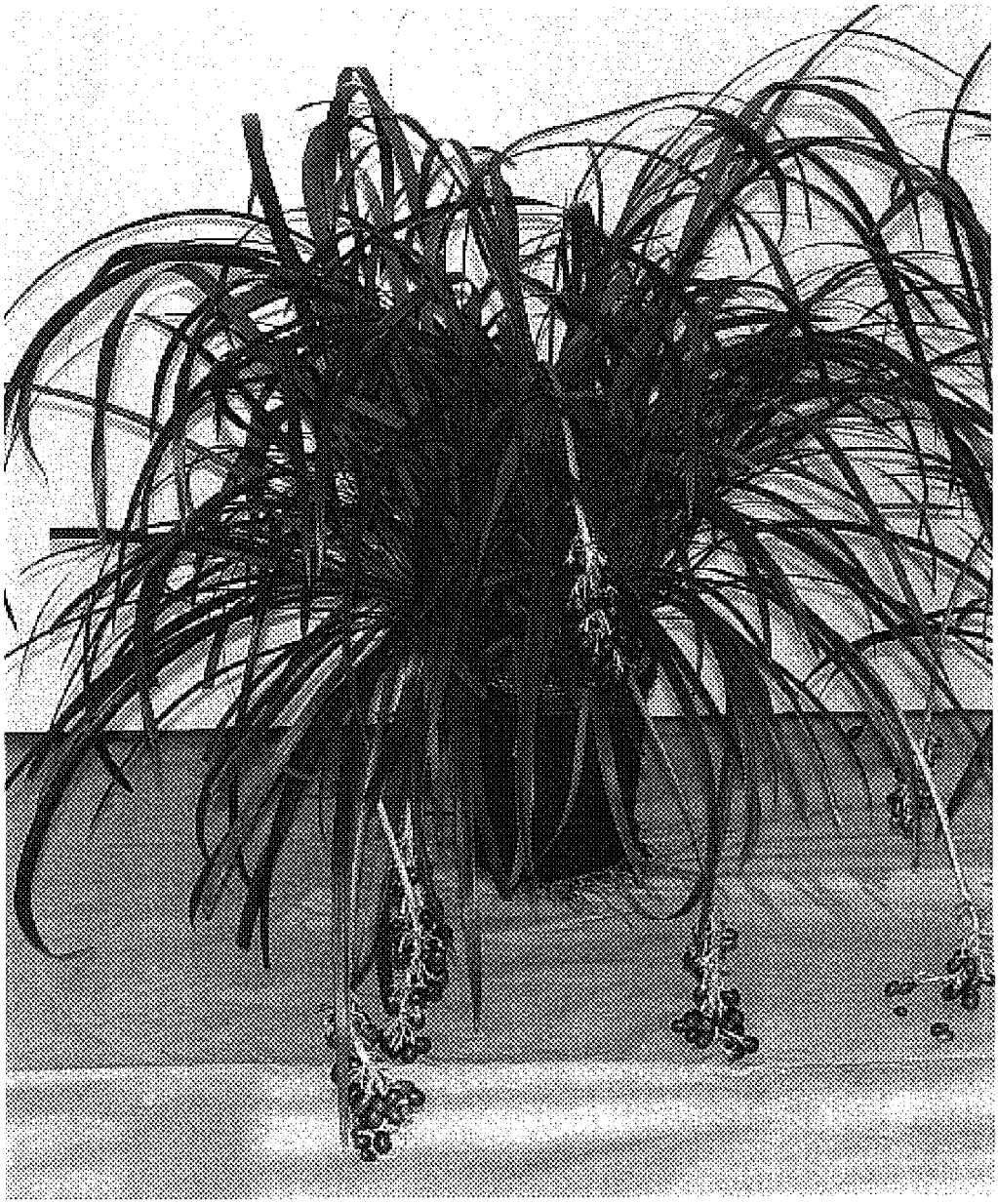

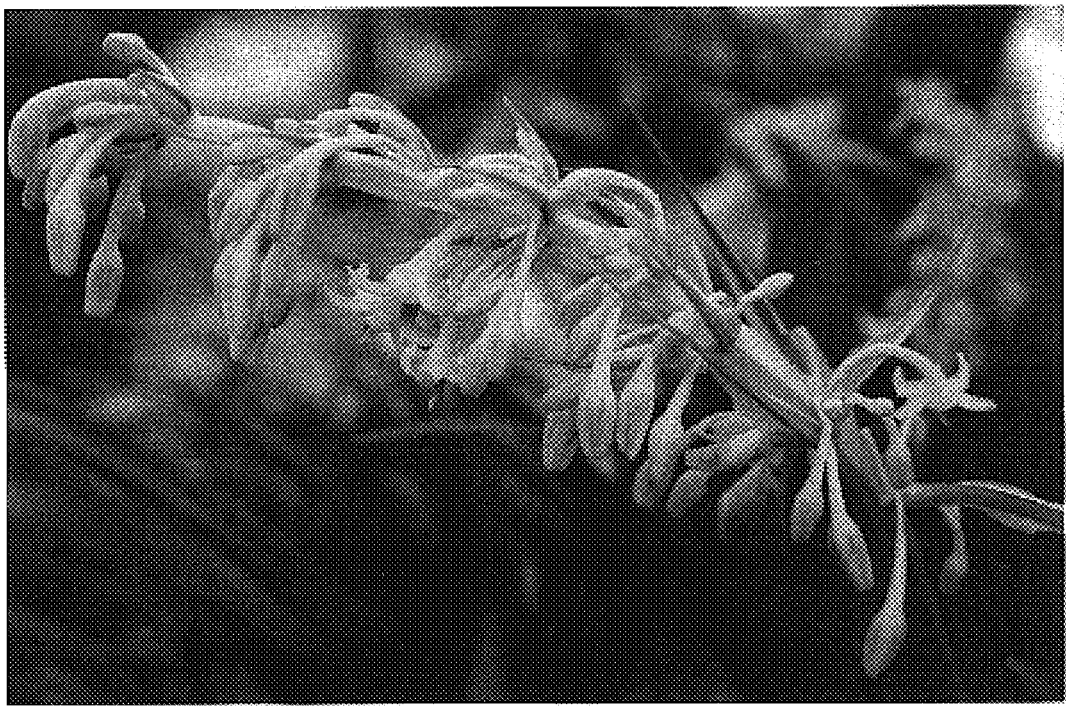

* * * * *